United States Patent [19]

Shida et al.

[11] Patent Number: 4,983,209
[45] Date of Patent: * Jan. 8, 1991

[54] 4,5-DIHYDRO-1H-1,2,4-TRIAZOLE-3-CARBOXAMIDE DERIVATIVES AND HERBICIDAL COMPOSITION CONTAINING THE SAME

[75] Inventors: Takafumi Shida; Yoshikazu Kubota; Isao Ichinose; Takeo Watanabe; Shiro Yamazaki; Hiroyasu Shinkawa, all of Iwaki, Japan

[73] Assignee: Kureha Kagaku Kogyo Kabushiki Kaisha, Tokyo, Japan

[ * ] Notice: The portion of the term of this patent subsequent to Jan. 30, 2007 has been disclaimed.

[21] Appl. No.: 169,465

[22] Filed: Mar. 17, 1988

[30] Foreign Application Priority Data

Mar. 27, 1987 [JP] Japan .................... 62-73709

[51] Int. Cl.⁵ .............. C07D 249/08; A01N 43/653
[52] U.S. Cl. ............................ 71/92; 548/266.8
[58] Field of Search .................. 71/92; 548/262

[56] References Cited

U.S. PATENT DOCUMENTS 4,820,334  7/1989  Shida et al. ............... 71/92

FOREIGN PATENT DOCUMENTS 189300   of 1986  European Pat. Off. ........... 548/262
2526271  of 1983  France ................... 548/262
61-171475  8/1986  Japan .
61-210075  9/1986  Japan .

*Primary Examiner*—Glennon H. Hollrah
*Assistant Examiner*—Patricia L. Morris
*Attorney, Agent, or Firm*—Nixon & Vanderhye

[57] ABSTRACT

Disclosed herein is a 4,5-dihydro-1H-1,2,4-triazole-3-carboxamide derivative represented by the formula (I):

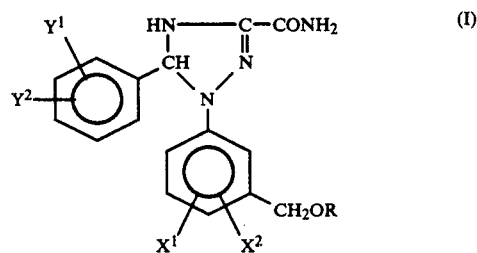

wherein R represents a straight-chain alkyl group having 1 to 10 carbon atoms which is non-substituted or substituted with 1 to 19 fluorine atoms or a branched alkyl group having 3 to 10 carbon atoms which is non-substituted or substituted with 1 to 19 fluorine atoms; $X^1$ represents a halogen atom or an alkyl group having 1 to 3 carbon atoms; $X^2$ represents hydrogen atom, a halogen atom or an alkyl group having 1 to 3 carbon atoms; $Y^1$ represents hydrogen atom or fluorine atom; and $Y^2$ represents hydrogen atom or fluorine atom. The derivatives of the formula (I) have high herbicidal activities and also show a excellent selectivity in their actions for killing weeds alone while doing any practical harm to the crops such as rice, wheat and corn.

7 Claims, No Drawings

4,5-DIHYDRO-1H-1,2,4-TRIAZOLE-3-CARBOXAMIDE DERIVATIVES AND HERBICIDAL COMPOSITION CONTAINING THE SAME

BACKGROUND OF THE INVENTION

The present invention relates to 4,5-dihydro-1H-1,2,4-triazole-3-carboxamide derivatives useful as active ingredient of herbicides and the herbicidal compositions containing such derivatives.

Rice, wheat and corn are the important farm products, and use of herbicides is essential for protecting these crops from harm by weeds to achieve an increased yield of the crops.

Few reports have been published relating to 4,5-dihydro-1H-1,2,4-triazole-3-carboxylic acid derivatives. Only disclosures relating to such derivatives were made in Japanese Patent Application Kokai (Laid-Open) Nos. 171475/86 and 210075/86 in which there are disclosed the compounds represented by the formula (I'):

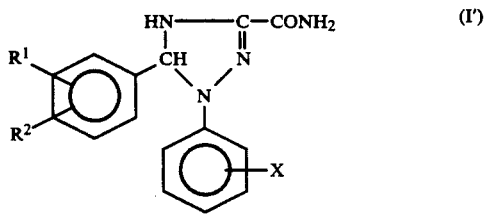

wherein X represents H, 3-CH$_3$ or 4-Cl; R$^1$ represents H; and R$^2$ represents H, 4-Cl, 4-OH, 2-OH, 2-COOH, 3-CH$_3$ or 3-OH.

In Japanese Patent Application Kokai (Laid-Open) No. 210075/86, mention is made of the herbicidal activity of the compounds represented by the formula (I'), but actually such compounds are unsatisfactory in their herbicidal effect. Thus, the development of a compound showing a high herbicidal activity and also having an effective selectivity in its action for killing weeds alone without doing any practical harm to the crops such as rice, wheat and corn has been strongly desired.

As a result of the present inventors' studies for providing a compound showing an excellent herbicidal effect and giving no practical harm to such crops as rice, wheat and corn, the present inventors found that the 4,5-dihydro-1H-1,2,4-triazole-3-carboxamide derivatives represented by the following formula (I) have an excellent selective herbicidal effect and achieved the present invention based on this finding:

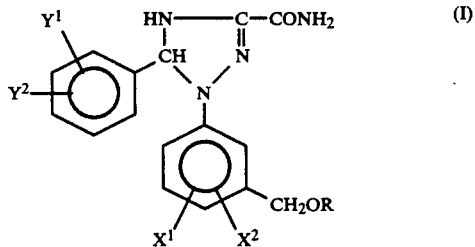

wherein R represents a straight-chain alkyl group having 1 to 10 carbon atoms which is non-substituted or substituted with 1 to 19 fluorine atoms or a branched alkyl group having 3 to 10 carbon atoms which is non-substituted or substituted with 1 to 19 fluorine atoms; X$^1$ represents a halogen atom or an alkyl group having 1 to 3 carbon atoms; X$^2$ represents hydrogen atom, a halogen atom or an alkyl group having 1 to 3 carbon atoms; Y$^1$ represents hydrogen atom or fluorine atom; and Y$^2$ represents hydrogen atom or fluorine atom.

The compounds represented by the formula (I) are different from the compounds of the formula (I') disclosed in Japanese Patent Application Kokai (Laid-Open) Nos. 171475/86 and 210075/86 in that the former have a side chain of —CH$_2$OR (wherein R represents the same as defined in the formula (I)) in the phenyl at the 1-position of 4,5-dihydro-1H-1,2,4-triazole, and are not found in the prior art literatures.

Thus, the object of the present invention is in providing the 4,5-dihydro-1H-1,2,4-triazole-3-carboxamide derivatives which have excellent selective herbicidal potencies, i.e., showing strong herbicidal activities against gramineous weeds and broadleaf plants, in particular, broadleaf plants, but quite hermless to the crops such as rice, wheat and corn, and the herbicidal compositions containing such compounds as active ingredient.

SUMMARY OF THE INVENTION

In a first aspect of the present invention, there is provided a 4,5-dihydro-1H-1,2,4-triazole-3-carboxamide derivative represented by the formula (I):

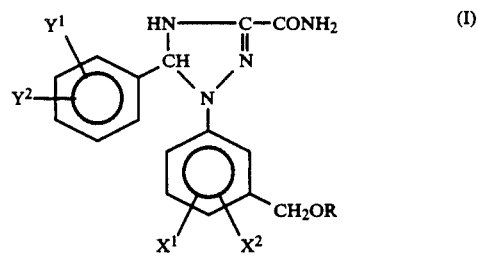

wherein R represents a straight-chain alkyl group having 1 to 10 carbon atoms which is non-substituted or substituted with 1 to 19 fluorine atoms or a branched alkyl group having 3 to 10 carbon atoms which is non-substituted or substituted with 1 to 19 fluorine atoms; X$^1$ represents a halogen atom or an alkyl group having 1 to 3 carbon atoms; X$^2$ represents hydrogen atom, a halogen atom or an alkyl group having 1 to 3 carbon atoms; Y$^1$ represents hydrogen atom or fluorine atom; and Y$^2$ represents hydrogen atom or fluorine atom.

In a second aspect of the present invention, there is provided a herbicidal composition comprising as active ingredient a herbicidally effective amount of 4,5-dihydro-1H-1,2,4-triazole-3-carboxamide derivative represented by the formula (I):

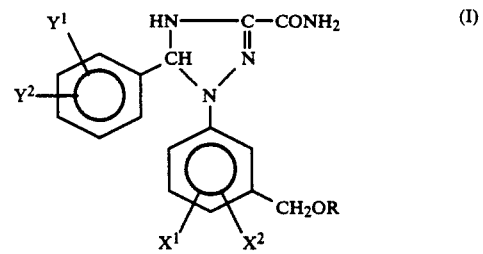

wherein R represents a straight-chain alkyl group having 1 to 10 carbon atoms which is non-substituted or substituted with 1 to 19 fluorine atoms or a branched alkyl group having 3 to 10 carbon atoms which is non-substituted or substituted with 1 to 19 fluorine atoms; $X^1$ represents a halogen atom or an alkyl group having 1 to 3 carbon atoms; $X^2$ represents hydrogen atom, a halogen atom or an alkyl group having 1 to 3 carbon atoms; $Y^1$ represents hydrogen atom or fluorine atom; and $Y^2$ represents hydrogen atom or fluorine atom, and herbicidally acceptable carrier or adjuvant.

In a third aspect of the present invention, there is provided a process for producing 4,5-dihydro-1H-1,2,4-triazole-3-carboxamide derivatives represented by the formula (I):

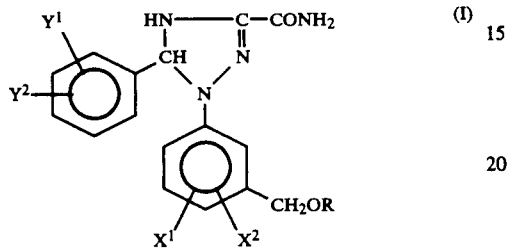

wherein R represents a straight-chain alkyl group having 1 to 10 carbon atoms which is non-substituted or substituted with 1 to 19 fluorine atoms or a branched alkyl group having 3 to 10 carbon atoms which is non-substituted or substituted with 1 to 19 fluorine atoms; $X^1$ represents a halogen atom or an alkyl group having 1 to 3 carbon atoms; $X^2$ represents hydrogen atom, a halogen atom or an alkyl group having 1 to 3 carbon atoms; $Y^1$ represents hydrogen atom or fluorine atom; and $Y^2$ represents hydrogen atom or fluorine atom, which comprises subjecting an oxamide derivative represented by the formula (II):

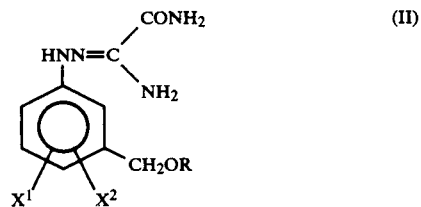

wherein R, $X^1$ and $X^2$ are as defined above, and a benzaldehyde derivative represented by the formula (III):

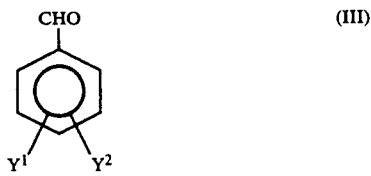

wherein $Y^1$ and $Y^2$ are as defined above, to a dehydrating-condensation reaction in the presence of an acid catalyst.

DETAILED DESCRIPTION OF THE INVENTION

The present invention relates to the 4,5-dihydro-1H-1,2,4-triazole-3-carboxamide derivative represented by the formula (I):

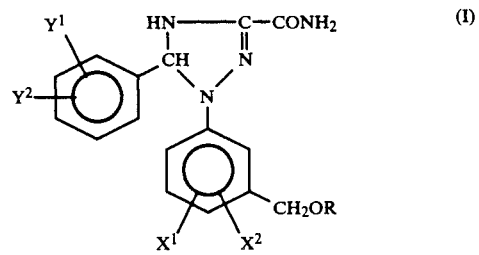

and the herbicidal composition containing said compounds as active ingredient.

In the formula (I), R represents a straight-chain alkyl group having 1; to 10, preferably 3 to 6 carbon atoms, which is non-substituted or substituted with 1 to 19, preferably 3 to 12 fluorine atoms, or a branched alkyl group having 3 to 10, preferably 3 to 6 carbon atoms, which is non-substituted or substituted with 1 to 19, preferably 3 to 12 fluorine atoms, $X^1$ represents a halogen atom or an alkyl group having 1 to 3 carbon atoms. $X^2$ represents hydrogen atom, a halogen atom or an alkyl group having 1 to 3 carbon atoms. Both of $Y^1$ and $Y^2$ independently represent hydrogen atom or fluorine atom.

Typical examples of the compounds represented by the formula (I) according to the present invention and their physicochemical properties are shown in Table 1.

TABLE 1

| No. | R | $X^1$ | $X^2$ | $Y^1$ | $Y^2$ | Yield of synthesis (%) | Melting point (°C.) | NMR spectrum (CDCl$_3$-DMSO-d$_6$, δ, ppm, 60 MHz) |
|---|---|---|---|---|---|---|---|---|
| 1 | CH$_2$CH$_2$CH(CH$_3$)CH$_3$ | 4-Cl | H | 2-F | 6-F | 95.0 | 188–190 | 0.90(6H,d,6Hz) 1.2–2.0(3H,m) 3.43(2H,t, 6Hz) 4.37(2H,s) 6.7–7.7(10H,m) |
| 2 | CH$_2$CH$_2$CH(CH$_3$)CH$_3$ | 4-Cl | H | 2-F | 4-F | 90.7 | 170–171 | 0.93(6H,d,6Hz) 1.3–2.0(3H,m) 3.47(2H,t, 6Hz) 4.43(2H,s) 6.63(1H,s) 6.7–7.8(9H,m) |
| 3 | CH$_2$CH$_2$CH(CH$_3$)CH$_3$ | 2-Cl | 4-Cl | H | H | 83.8 | 113–115 | 0.83(6H,d,6Hz) 1.2–2.0(3H,m) 3.37(2H,t, 6Hz) 4.65(2H,s) 5.83(1H,bs) 6.03(1H,bs) 6.75(1H,s) 6.7–7.5(8H,m) |

TABLE 1-continued

| No. | R | X¹ | X² | Y¹ | Y² | Yield of synthesis (%) | Melting point (°C.) | NMR spectrum (CDCl$_3$-DMSO-d$_6$, δ, ppm, 60 MHz) |
|---|---|---|---|---|---|---|---|---|
| 4 | CH$_2$CH$_2$CH(CH$_3$)CH$_3$ | 4-Cl | 6-Cl | H | H | 77.8 | 180–182 | 0.90(6H,d,6Hz) 1.2–2.0(3H,m) 3.43(2H,t,6Hz) 4.30(2H,s) 6.80(1H,s) 6.9(2H,bs) 7.20(1H,s) 7.1–7.4(6H,m) 7.50(1H,s) |
| 5 | CH$_2$CH$_2$CH(CH$_3$)CH$_3$ | 4-CH$_3$ | H | 2-F | 6-F | 91.3 | 174–177 | 0.89(6H,d,6.8Hz) 1.48(2H,q,6.8Hz) 1.71(1H,9-plet,6.8Hz) 2.18(3H,s) 3.44(2H,t,6.8Hz), 4.38(2H,s) 5.23(1H,bs) 5.34(1H,bs) 6.66 (1H,bs) 6.76)1H,dd,7.8Hz,2.0Hz) 6.87(2H, t,8.5Hz) 6.95–7.01(2H,m) 7.03(1H,s) 7.2–7.35(1H,m)** |
| 6 | CH$_2$CF$_2$CF$_3$ | 4-CH$_3$ | H | 2-F | 6-F | 91.2 | 182–185 | 2.19(3H,s) 3.78(2H,tq,13.2Hz, 1.5Hz) 4.54 (1H,d,12Hz) 4.59(1H,d,12Hz) 5.29(1H,bs) 5.38(1H,bs) 6.67(1H,bs) 6.88(1H,dd,8.3Hz, 2.7Hz) 6.88(2H,t,8.5Hz) 6.92(1H,d,2.7Hz) 7.01(1H,d,8.3Hz) 7.04(1H,s) 7.2–7.35(1H,m)** |
| 7 | CH$_2$CF$_2$CF$_3$ | 4-Cl | H | H | H | 73.9 | 176–178 | 3.87(2H,tq,13Hz,1Hz) 4.55(2H,s) 6.33(1H,s) 6.7–7.7(11H,m) |
| 8 | CH$_2$CF$_2$CF$_3$ | 4-Cl | H | 2-F | H | 81.2 | 176–178 | 3.93(2H,tq,13Hz,1Hz) 4.60(2H,s) 6.70(1H,s) 6.9–7.7(11H,m) |
| 9 | CH$_2$CF$_2$CF$_3$ | 4-CH$_3$ | H | H | H | 78.4 | 178–180 | 2.18(3H,s) 3.75(2H,tq,11.2Hz,1.0Hz) 4.55 (2H,s) 5.35(2H,bs) 6.62(1H,bs) 6.38(1H,s) 6.72(1H,dd,8.8Hz,2.4Hz) 6.89(1H,d,2.4Hz) 6.98(1H,d,8.8Hz) 7.3–7.6(5H,m)** |
| 10 | CH$_2$CF$_2$CF$_3$ | 4-CH$_3$ | H | 2-F | H | 92.8 | 165–167 | 2.20(3H,s) 3.80(2H,tq,12.0Hz,1.0Hz) 4.58 (2H,s) 5.37(1H,bs) 5.48(1H,bs) 6.63(1H,bs) 6.74(1H,dd,7.8Hz,2.0Hz) 6.75(1H,s) 6.92 (1H,d,2.0Hz) 7.02(1H,d,7.8Hz) 7.05–7.6 (4H,m)** |
| 11 | CH$_2$CH$_2$CH(CH$_3$)CH$_3$ | 4-Cl | H | H | H | 90.5 | 174–176 | 0.87(6H,d,7Hz) 1.2–2.0(3H,m) 3.40(2H,t,7Hz) 4.37(2H,s) 6.30(1H,s) 6.7–7.6(11H,m) |
| 12 | CH$_2$CH$_2$CH(CH$_3$)CH$_3$ | 4-Cl | H | 2-F | H | 86.4 | 170–171 | 0.87(6H,d,6Hz) 1.1–2.2(3H,m) 3.40(2H,t,6Hz) 4.37(2H,s) 6.63(1H,s) 6.7–7.7(10H,m) |
| 13 | CH$_2$CH$_2$CH(CH$_3$)CH$_3$ | 4-CH$_3$ | H | H | H | 75.6 | 168–170 | 0.88(6H,d,6.8Hz) 1.45(2H,q,6.8Hz) 1.68(1H, 9-plet,6.8Hz) 2.18(3H,s) 3.42(2H,t,6.8Hz) 4.35 (1H,d,12Hz) 4.38(1H,d,12Hz) 5.32(2H, bs) 6.63(1H,bs) 6.37(1H,s) 6.68(1H,dd, 7.8Hz,2.0Hz) 6.9–7.0(2H,m) 7.3–7.5(5H,m)** |
| 14 | CH$_2$CH$_2$CH(CH$_3$)CH$_3$ | 4-CH$_3$ | H | 2-F | H | 95.4 | 151.5–153 | 0.87(6H,d,6.8Hz) 1.45(2H,q,6.8Hz) 1.68(1H, 9-plet,6.8Hz) 2.20(3H,s) 3.44(2H,t,6.8Hz) 4.39(2H,s) 5.33(1H,bs) 5.45(1H,bs) 6.63 (1H,bs) 6.71(1H,dd,7.8Hz,2.4Hz) 6.74(1H, s) 6.97(1H,d,2.4Hz) 6.98(1H,d,7.8Hz) 7.02–7.5(4H,m)** |
| 15 | CH$_2$CF$_3$ | 4-Cl | H | H | H | 84.0 | 178–180 | 3.92(2H,q,9Hz) 4.59(2H,s) 6.34(1H,d,2Hz) 6.6–7.6(11H,m)*** |
| 16 | CH$_2$CF$_2$CF$_2$CF$_3$ | 4-Cl | H | H | H | 86.5 | 157–159 | 4.03(2H,tt,14Hz,2Hz) 4.58(2H,s) 6.33(1H, d,2Hz) 6.5–7.7(11H,m)*** |

*Numbering of the substituents followed the following formula.

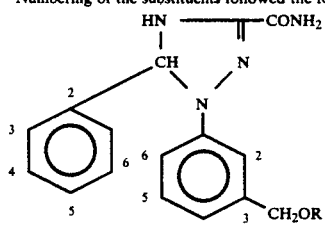

**Measured by a 250 MHz apparatus using CDCl$_3$ as solvent.
***DMSO-d$_6$ was used as solvent.

All of these compounds, owing to their excellent selective herbicidal activities such as mentioned above, The compounds of the present invention represented by the formula (I) can be synthesized very easily from a reaction according to the following Reaction Scheme 1.

Reaction Scheme 1

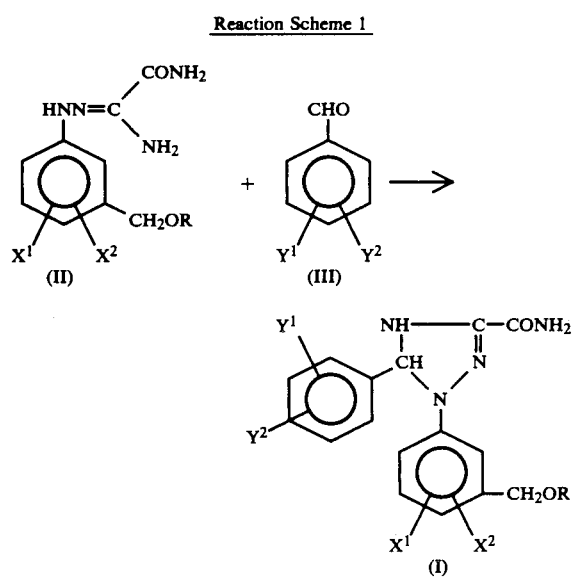

wherein R, $X^1$, $X^2$, $Y^1$ and $Y^2$ are as defined above

An oxamide derivative of the formula (II) and a benzaldehyde derivative of the formula (III) are subjected to a dehydrating-condensation reaction in the presence of an acid catalyst such as acetic acid, p-toluenesulfonic acid, etc., at a temperature of preferably 0° to 150° C. for 0.1 to 40 hours. When the reaction is carried out in an inert gas atmosphere, the yield of synthesis increases.

The oxamide derivative (11) used as a starting material for the synthesis of the compounds of the present invention can be synthesized through the reactions according to the following Reaction Scheme 2.

Reaction Scheme 2

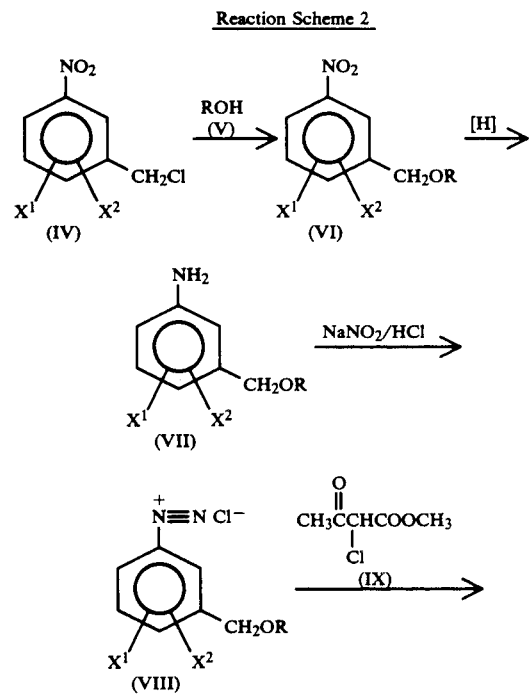

-continued
Reaction Scheme 2

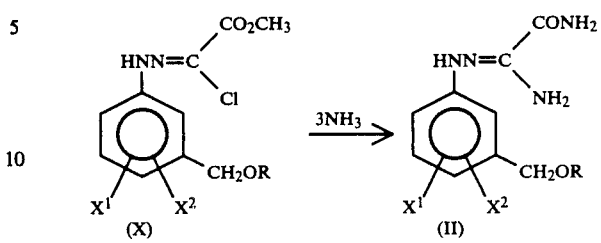

wherein R, $X^1$ and $X^2$ are as defined above.

A derivative of 3-nitrobenzyl chloride (IV) and a compound of the formula (V) are reacted in a solvent such as dimethylformamide, hexamethylphosphoramide, etc., in the presence of a hydrogen chloride acceptor such as KOH, NaH, etc., at a temperature in the range from −10° to 150° C., preferably from 0° to 80° C., for 0.1 to 20 hours, preferably 0.5 to 10 hours, to obtain a nitrobenzene derivative of the formula (VI). This nitrobenzene derivative is reduced into an aniline derivative (VII) by a conventional method, for example, by adding hydrazine hydrate to said nitrobenzene derivative in an alcohol and heating the solution under reflux in the presence of palladium-charcoal for 1 to 10 hours.

Other reduction methods usable here include a method in which the nitrobenzene derivative is reduced by using iron, zinc, tin or the like in a solvent such as hydrochloric acid, acetic acid, etc.; a method in which the nitrobenzene derivative is reduced with colloidal sulfur or sodium sulfide in ethanol or hydrous ethanol; a method in which the nitrobenzene derivative is reduced by the action of hydrazine in ethanol in the presence of a ferric salt and active carbon or in the presence of palladium carbon; and a catalytic reduction method where reduction is carried out with hydrogen of normal pressure to 5 atom in a solvent such as ethanol or acetic acid in the presence of a catalyst such as Raney nickel, palladium carbon, platinum oxide, etc.

Then the aniline derivative (VII) is converted into a diazonium salt (VIII) in, for instance, hydrochloric acid at −10° to 15° C. by using sodium nitrite and this diazonium salt (VIII) is reacted with a 2-chloroaceto acetic acid ester (IX) at −10° to 50° C., preferably 0° to 30° C., in a solvent such as aqueous ethanol in the presence of a base such as sodium acetate, sodium bicarbonate, etc. This reaction gives a chloro(arylhydrazono)acetic acid ester of the formula (X). Finally, the compound of the formula (X) is reacted with ammonia in an alcohol such as methanol or ethanol at −10° to 50° C., preferably 0° to 30° C., to give an oxamide derivative (II) which is used as a starting material for the synthesis of the compounds of the present invention.

The 4,5-dihydro-1H-1,2,4-triazole-3-carboxamide derivative of the present invention can be used either independently or as mixtures with a wide variety of carriers (diluents) and/or adjuvants commonly used in the preparation of agricultural chemicals, in the form of compositions such as wettable powder, emulsion, granules, powder, etc.

The concentration of 4,5-dihydro-1H-1,2,4-triazole-3-carboxamide derivative of the present invention in herbicidal compositions is preferably in the range of 0.1 to 50% by weight.

The 4,5-dihydro-1H-1,2,4-triazole-3-carboxamide derivative of the present invention and the herbicidal composition containing the compound of the present invention as active ingredient are sprayed on the soil of crop fields and paddy fields and/or to the stalks and leaves of plants by a conventional method so that the compound will be applied at a rate of 0.1 to 500 g per 10 ares.

The present invention will hereinafter be described more precisely while referring to the following non-limitative examples.

SYNTHESIS EXAMPLE 1

Synthesis of 3-(2,2,3,3,3-pentafluoropropoxy)methyl-4-methyl-1-nitrobenzene (compound of formula (VI) wherein $R=CH_2CF_2CF_3$, 4-$CH_3$ and $X^2=H$)

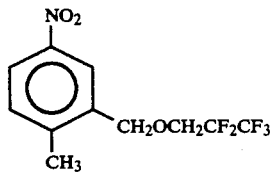

In 16.5 ml of dimethylformamide, 5.00 g (0.027 mol) of 2-methyl-5-nitrobenzyl chloride and 21.3 g (0.135 mol) of 2,2,3,3,3-pentafluoropropanol were dissolved. The solution was then added with 2.29 g (0.041 mol) of KOH pellets and stirred overnight. Dichloromethane was added and the precipitated salts were filtered out. The filtrate was acidified with dilute hydrochloric acid and then the solvents were distilled off.

The residue was dissolved in a 9/1 mixed solvent of hexane and ethyl acetate, washed with dilute hydrochloric acid, water and a saturated sodium chloride solution, and then dried over magnesium sulfate. The solvent was distilled off and the resulting oil was purified by silica gel chromatography using hexane/ethyl acetate (19/1, v/v) as developing solvent to obtain 7.71 g of the desired product (m.p. 53.5°-54.5° C.) in a 95.5% yield.

SYNTHESIS EXAMPLE 2

Synthesis of 3-(2,2,3,3,3-pentafluoropropoxy)methyl-4-methylaniline (compound of formula (VII) wherein $R=CH_2CF_2CF_3$, $X^1=4$-$CH_3$ and $X^2=H$)

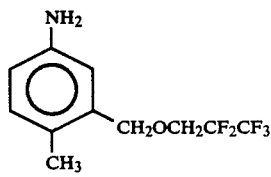

In 40 ml of ethanol, 7.30 g (0.0244 mol) of 3-(2,2,3,3,3-pentafluoropropoxy)methyl-4-methyl-1-nitrobenzene obtained in Synthesis Example 1 was dissolved. The solution was added with 0.1 g of 10% Pd-C and 3.66 g (0.073 mol) of hydrazine hydrate and refluxed on a hot water bath for one hour. After allowed to cool, the solution was filtered through a celite layer to remove the catalyst and then washed with ethanol. The filtrate was concentrated, dissolved in dichloromethane, washed with water, a saturated sodium bicarbonate solution and a saturated sodium chloride solution successively and then dried over anhydrous potassium carbonate. The solvents were distilled off and the residue was distilled fractionally, collecting the fraction of a boiling point of 82°-83° C. (at 0.18 mmHg) to obtain 6.09 g of the desired product in a 93% yield.

SYNTHESIS EXAMPLE 3

Synthesis of methyl chloro [3-(2,2,3,3,3-pentafluoropropoxy)-methyl-4-methylphenylhydrazono]acetate (compound of formula (X) wherein $R=CH_2CF_2CF_3$, $X^1=4$—$CH_3$ and $X^2=H$)

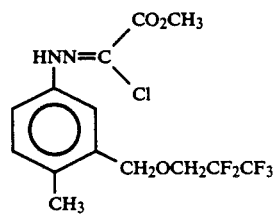

In a mixture of 3 ml of acetic acid and 1.2 ml of concentrated hydrochloric acid, 1.417 g (5.3 mmol) of aniline derivative obtained in Synthesis Example 2 was dissolved. Then an aqueous solution (1.1 ml) of 381 mg of sodium nitrite was added dropwise at −5° to 0° C. to prepare a diazonium salt solution.

Separately, 832 mg (5.5 mmol) of methyl 2-chloroacetoacetate was added to a mixture of 2.5 ml of ethanol, 3.1 ml of water and 1.175 g (14.3 mmol) of sodium acetate and cooled to 0° C. To this solution was added the diazonium salt solution, and the mixed solution was stirred at 0° C. for 30 minutes and then at room temperature for 2 hours. The resulting solution was diluted with water and extracted with dichloromethane. The organic layer was washed with water and a saturated sodium chloride solution and dried over magnesium sulfate. The solvents were distilled off to obtain 1.868 g (91.3% yield) of the desired product as a light-orange oil.

SYNTHESIS EXAMPLE 4

Synthesis of oxamide 3-(2,2,3,3,3-pentafluoropropoxy)-methyl-4-methylphenylhydrazone (compound of formula (II) wherein $R=CH_2CF_2CF_3$, $X^1=4$—$CH_3$ and $X^2=X$)

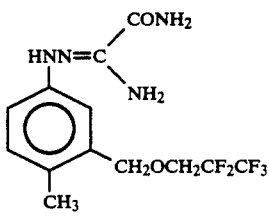

A 10 ml dichloromethane solution of 1.748 g (4.5 mmol) of chloroacetic acid ester derivative obtained in Synthesis Example 3 was added to 10 ml of an ammonia-methanol solution (with 20% ammonia content). The solution was stirred at room temperature for 30 minutes and left overnight while stoppered tightly. The solvents were distilled off and the residue was added with water and dichloromethane. The organic layer was separated, washed with water and then with a saturated sodium chloride solution and dried over anhydrous sodium sulfate. The solvent was distilled off and the resulting crude crystals were purified by silica gel chromatography using ethyl acetate/ n-hexane (1/1, v/v) as developing solvent and further recrystallized from dichloromethane/n-hexane to obtain 1.332 g of white crystals (m.p. 129°–130° C.) in a 83.6% yield.

EXAMPLE 1

Synthesis of 5-(2,6-difluorophenyl)-1-[3-(2,2,3,3,3-pentafluoropropoxy)methyl-4-methylphenyl]-4,5-dihydro-1H-1,2,4-triazole-3-carboxamide (Compound No. 6)

In 2.8 ml of acetic acid, 502 mg (1.42 mmol) of oxamide derivative obtained in Synthesis Example 4 was dissolved and nitrogen was saturated. The solution was added with 2,6-difluorobenzaldehyde under a nitrogen atmosphere and stirred at room temperature for 16 hours. Then water was added to the solution and the precipitated crystals were filtered out, washed with water and dried in vacuo.

The resulting product was recrystallized from acetone/dichloromethane/n-hexane with nitrogen saturated to obtain 618 mg (91.2% yield) of 5-(2,6-difluorophenyl) 1-[3-(2,2,3,3,3-pentafluoropropoxy)methyl-4-methylphenyl]-4,5-dihydro-1H-1,2,4-triazole-3-carboxamide (m.p. 182°–185° C.).

EXAMPLE 2

Synthesis of 1-[4-chloro-3-[(3-methylbutoxy)methyl]phenyl]-4,5-dihydro-5-phenyl-1H-1,2,4-triazole-3-carboxamide (Compound No. 11)

In 2.0 ml of acetic acid 500 mg (1.6 mmol) of oxamide 4-chloro-3-[(3-methylbutoxy)methyl]phenylhydrazone obtained in the same manner as Synthesis Examples 1–4 was dissolved and nitrogen was saturated. The solution was added with 187 mg (1.8 mmol) of benzaldehyde under a nitrogen atmosphere and stirred at room temperature for 18 hours. Then water was added to the solution and the produced precipitate was crushed and filtered out. The crystals were washed with 50% hydrous acetic acid and then with water and dried in vacuo. The resulting product was recrystallized from ethyl acetate/n-hexane with nitrogen saturated to obtain 581 mg (90.5% yield) of 1-[4-chloro-3-[(3-methylbutoxy)methyl]phenyl]-4,5-dihydro-5-phenyl-1H-1,2,4-triazole3-carboxamide (m.p. 174°–176° C.).

EXAMPLE 3

Synthesis of 1-[4-chloro-3-[(2,2,3,3,4,4,4-heptafluorobutoxy)methyl]phenyl]-4,5-dihydro-5-phenyl-1H-1,2,4-triazole-3-carboxamide (Compound No. 16)

In 0.7 ml of acetic acid, 245 mg (0.6 mmol) of oxamide 4-chloro-3-[(2,2,-3,3,4,4,4-heptafluorobutoxy)methyl]phenylhydrazone was dissolved and nitrogen was saturated. The solution was added with 76 mg (0.72 mmol) of benzaldehyde under a nitrogen atmosphere and stirred at room temperature for 16 hours. Then water was added to the solution and the formed crystals were filtered out, washed with water and dried in vacuo. The resulting product was recrystallized from ethyl acetate/n-hexane with nitrogen saturated to obtain 257 mg (86.5% yield) of 1-[4-chloro-3-][(2,2,3,3,4,4,4-heptafluorobutoxy)methyl]phenyl]-4,5-dihydro-5-phenyl-1H-1,2,4-triazole-3-carboxamide (m.p. 157°–159° C.).

EXAMPLE 4

Preparation of wettable powder

Fifty parts of Compound No. 7 (see Table 1), 5 parts of a salt of lignin sulfonic acid, 3 parts of a salt of alkylsulfonic acid and 42 parts of diatomaceous earth are mixed and pulverized to prepare a wettable powder. This wettable powder is diluted with water when used.

EXAMPLE 5

Preparation of emulsion

Twenty-five parts of Compound No.9 (see Table 1), 65 parts of xylene and 10 parts of polyoxyethylene alkylaryl ether are uniformly mixed to prepare an emulsion. This emulsion is diluted with water when used.

EXAMPLE 6

Preparation of granules

Eight parts of Compound No. 16 (see Table 1), 40 parts of bentonite, 45 parts of clay and 7 parts of a salt of lignin sulfonic acid are uniformly mixed and the mixture is kneaded by adding water, granulated by an extrusion granulator and dried.

It is possible to obtain the wettable powders, emulsions and granules in the same way as Examples 4–6 by using other compounds of the present invention.

The Test Examples are given below to show the selective herbicidal activities of the 4,5-dihydro-1H1,2,4-triazole-3-carboxamide derivative of the present invention.

TEST EXAMPLE 1

Effect of crop field weeds (pre-emergence treatment)

The seeds of various test plants shown in Table 2 were sown and covered with soil in the planters (65×210×220 mm) having soil placed therein in the manner of crop field. Then the wettable powders prepared in the same way as example 4 and diluted with water to a prescribed concentration were sprayed uniformly on the soil surface by a spraygun so that the active ingredient (compound) would be applied to the soil at a rate of 200 g/10 a. Then the planters were kept in a greenhouse to provide a favorable condition for the growth of the plants.

Twenty-one days after the treatment, the herbicidal effect of the compounds on the weeds and the phytotoxicity to the crops by the compounds were observed and evaluated according to the following ratings. The results are shown in Table 2.

Ratings for evaluation

0 . . . no herbicidal effect
1 . . . not more than 30% herbicidal effect
2 . . . 31–50% herbicidal effect
3 . . . 51–70% herbicidal effect
4 . . . 71–90% herbicidal effect
5 . . . 91–100% herbicidal effect Degree of phytotoxicity to crops −. . . none; ±. . . slight
+. . . medium; ++. . . great
+++. . . serious

TABLE 2

| Compound No. | Amaranthus retroflexus | Bidens pilosa var. pilosa | Brassica arvensis | Stellaria media | Solanum nigrum | Abutilon theophrasti | Echinochloa Crusgalli var. frumentacea | Digitaria sanguinalis | Wheat | Corn |
|---|---|---|---|---|---|---|---|---|---|---|
| 1  | 5 | 5 | 5 | 5 | 5 | 5 | 5 | 5 | — | ± |
| 2  | 5 | 5 | 5 | 5 | 5 | 5 | 5 | 5 | — | ± |
| 3  | 5 | 5 | 5 | 5 | 5 | 4 | 4 | 4 | — | — |
| 4  | 5 | 5 | 5 | 5 | 5 | 5 | 5 | 5 | — | ± |
| 5  | 5 | 5 | 5 | 5 | 5 | 5 | 5 | 5 | — | ± |
| 6  | 5 | 5 | 5 | 5 | 5 | 5 | 5 | 5 | — | ± |
| 7  | 5 | 5 | 5 | 5 | 5 | 5 | 5 | 5 | — | ± |
| 8  | 5 | 5 | 5 | 5 | 5 | 5 | 5 | 5 | — | ± |
| 9  | 5 | 5 | 5 | 5 | 5 | 5 | 5 | 5 | — | ± |
| 10 | 5 | 5 | 5 | 5 | 5 | 5 | 5 | 5 | — | ± |
| 11 | 5 | 5 | 5 | 5 | 5 | 5 | 5 | 5 | — | ± |
| 12 | 5 | 5 | 5 | 5 | 5 | 5 | 5 | 5 | — | ± |
| 13 | 5 | 5 | 5 | 5 | 5 | 5 | 5 | 5 | — | ± |
| 14 | 5 | 5 | 5 | 5 | 5 | 5 | 5 | 5 | — | ± |
| 15 | 5 | 5 | 5 | 5 | 5 | 5 | 5 | 5 | — | ± |
| 16 | 5 | 5 | 5 | 5 | 5 | 5 | 5 | 5 | — | ± |

TEST EXAMPLE 2

Effect on crop field weeds (postemergence treatment)

The seeds of the test plants shown in Table 3 were sown by following the procedure of Test Example 1. When the plants have grown to the 1-2 leaf-stage, the same wettable powders as used in Test Example 1 were sprayed uniformly to the stalks and leaves of the plants and on the soil surface by a spraygun so that the active ingredient would be applied at a rate of 200 g/10 a. Then the planters were again left in a greenhouse to facilitate growth of the plants.

Twenty-one days after the treatment, the same examination and evaluation as in Test Example 1 was made. The results are shown in Table 3.

TABLE 3

| Compound No. | Amaranthus retroflexus | Bidens pilosa var. pilosa | Brassica arvensis | Stellaria media | Solanum nigrum | Abutilon theophrasti | Echinochloa Crusgalli var. frumentacea | Digitaria sanguinalis | Wheat | Corn |
|---|---|---|---|---|---|---|---|---|---|---|
| 1  | 5 | 5 | 5 | 5 | 4 | 4 | 2 | 2 | — | ± |
| 2  | 5 | 5 | 5 | 5 | 4 | 3 | 2 | 2 | — | ± |
| 3  | 4 | 5 | 5 | 5 | 4 | 2 | 3 | 2 | — | — |
| 4  | 5 | 5 | 5 | 5 | 4 | 3 | 2 | 2 | — | — |
| 5  | 5 | 5 | 5 | 5 | 4 | 4 | 2 | 3 | — | ± |
| 6  | 5 | 5 | 5 | 5 | 5 | 5 | 4 | 4 | — | ± |
| 7  | 5 | 5 | 5 | 5 | 5 | 5 | 5 | 5 | — | ± |
| 8  | 5 | 5 | 5 | 5 | 5 | 5 | 5 | 4 | — | ± |
| 9  | 5 | 5 | 5 | 5 | 5 | 5 | 2 | 4 | — | ± |
| 10 | 5 | 5 | 5 | 5 | 5 | 5 | 3 | 4 | — | ± |
| 11 | 5 | 5 | 5 | 5 | 5 | 4 | 2 | 2 | — | ± |
| 12 | 5 | 5 | 5 | 5 | 5 | 5 | 2 | 2 | — | ± |
| 13 | 5 | 5 | 5 | 5 | 5 | 4 | 3 | 4 | — | ± |
| 14 | 5 | 5 | 5 | 5 | 5 | 4 | 4 | 3 | — | ± |
| 15 | 5 | 5 | 5 | 5 | 5 | 5 | 2 | 3 | — | ± |
| 16 | 5 | 5 | 5 | 5 | 5 | 5 | 5 | 5 | ± | + |

TEST EXAMPLE 3

Effect on paddy field weeds and phytotoxicity to crops

The seeds of *Echinochloa Crus-galli* var. *hispidula*, *Scirpus juncoides* subsp. *Hotarui*, *Alisma canaliculatum*, *Monochoria vaginalis* and *Cyperus difformis* were sown on the soil and the tubers of *Sagittaria pygmaea* and *Cyperus serotinus* were planted in the 1/2000-are Wagner pots in which paddy field soil and water had been placed in the manner of paddy field. Further, two seedlings of rice plants (variety: Sasanishiki) at the two leaf-stage were bedded out in each of the pots. After keeping the pots in a greenhouse for 3 days for allowing growth of the plants, the emulsions prepared in the same way as Example 5 and diluted properly were trickled down uniformly to the water surface in each pot so that the active ingredient would be applied at a rate of 200 g/10 a.

Twenty-one days after the treatment, the herbicidal effect and the degree of phytotoxicity to rice plants were examined and evaluated according to the same ratings as in Test Example 1. The results are shown in Table 4.

TABLE 4

| Compound No. | Echinochloa Crus-galli var. hispidula | Scirpus juncoides subsp. Hotarui | Alisma canaliculatum | Monochoria vaginalis | Cyperus difformis | Sagittaria pygmaea | Cyperus serotinus | rice plant |
|---|---|---|---|---|---|---|---|---|
| 1 | 5 | 5 | 5 | 5 | 5 | 5 | 5 | — |
| 2 | 5 | 5 | 5 | 5 | 5 | 4 | 5 | — |
| 3 | 5 | 4 | 5 | 5 | 5 | 4 | 5 | — |
| 4 | 5 | 4 | 5 | 5 | 5 | 5 | 5 | — |

TABLE 4-continued

| Compound No. | Echinochloa Crus-galli var. hispidula | Scirpus juncoides subsp. Hotarui | Alisma canaliculatum | Monochoria vaginalis | Cyperus difformis | Sagittaria pygmaea | Cyperus serotinus | rice plant |
|---|---|---|---|---|---|---|---|---|
| 5 | 5 | 5 | 5 | 5 | 5 | 5 | 5 | — |
| 6 | 5 | 5 | 5 | 5 | 5 | 5 | 5 | — |
| 7 | 5 | 5 | 5 | 5 | 5 | 5 | 5 | — |
| 8 | 5 | 5 | 5 | 5 | 5 | 5 | 5 | — |
| 9 | 5 | 5 | 5 | 5 | 5 | 5 | 5 | — |
| 10 | 5 | 5 | 5 | 5 | 5 | 5 | 5 | — |
| 11 | 5 | 5 | 5 | 5 | 5 | 5 | 5 | — |
| 12 | 5 | 5 | 5 | 5 | 5 | 5 | 5 | — |
| 13 | 5 | 5 | 5 | 5 | 5 | 5 | 5 | — |
| 14 | 5 | 5 | 5 | 5 | 5 | 5 | 5 | — |
| 15 | 5 | 5 | 5 | 5 | 5 | 5 | 5 | — |
| 16 | 5 | 5 | 5 | 5 | 5 | 5 | 5 | — |

What is claimed is:

1. A 4,5-dihydro-1H-1,2,4-triazole-3-carboxamide derivative represented by the formula (I):

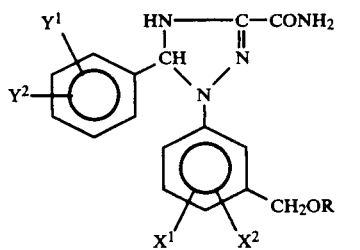

(I)

wherein R represents a straight-chain alkyl group having 1 to 10 carbon atoms which is non-substituted or substituted with 1 to 19 fluorine atoms or a branched alkyl group having 3 to 10 carbon atoms which is non-substituted or substituted with 1 to 19 fluorine atoms; $X^1$ represents a halogen atom or an alkyl group having 1 to 3 carbon atoms; $X^2$ represents hydrogen atom, a halogen atom or an alkyl group having 1 to 3 carbon atoms; $Y^1$ represents hydrogen atom or fluorine atom; and $Y^2$ represents hydrogen atom or fluorine atom.

2. The derivative according to claim 1, wherein said derivative is represented by the formula (I):

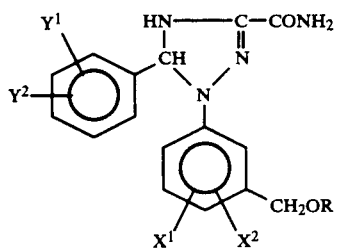

(I)

wherein R represents a straight-chain alkyl group having 3 to 6 carbon atoms which is non-substituted or substituted with 3 to 12 fluorine atoms or a branched alkyl group having 3 to 6 carbon atoms which is non-substituted or substituted with 3 to 12 fluorine atoms; $X^1$ represents a halogen atom or an alkyl group having 1 to 3 carbon atoms; $X^2$ represents hydrogen atom, a halogen atom or an alkyl group having 1 to 3 carbon atoms; $Y^1$ represents hydrogen atom or fluorine atom; and $Y^2$ represents hydrogen atom or fluorine atom.

3. The derivative according to claim 2, wherein said derivative is represented by the formula (I):

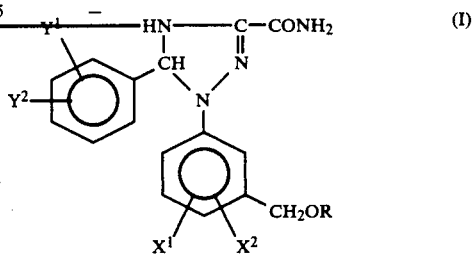

(I)

wherein R represents a straight-chain alkyl group having or 4 carbon atoms which is substituted with 5 to 7 fluorine atoms; $X^1$ represents a chlorine atom or a methyl group; and $X^2$, $Y^1$ and $Y^2$ respectively represent hydrogen atom.

4. The derivative according to claim 3, wherein said derivative is 1-[4-chloro-3-[(2,2,3,3,3-pentafluoropropoxy)methyl]phenyl]-4,5-dihydro-5-phenyl-1H-1,2,4-triazole-3-carboxamide.

5. The derivative according to claim 3, wherein said derivative is 1-[4-methyl-3-[(2,2,3,3,3-pentafluoropropoxy)methyl]phenyl]-4,5-dihydro-5-phenyl-1H-1,2,4-triazole-3-carboxamide.

6. The derivative according to claim 3, wherein said derivative is 1-[4-chloro-3-[(2,2,3,3,4,4,4-heptafluorobutoxy)methyl]phenyl]-4,5-dihydro-5-phenyl-1H-1,2,4-triazole-3-carboxamide.

7. A herbicidal composition comprising as active ingredient a herbicidally effective amount of 4,5-dihydro-1H-1,2,4-triazole-3-carboxamide derivative represented by the formula (I):

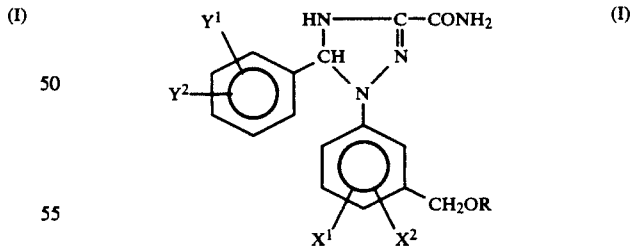

(I)

wherein R represents a straight-chain alkyl group having 1 to 10 carbon atoms which is non-substituted or substituted with 1 to 19 fluorine atoms or a branched alkyl group having to 10 carbon atoms which is non-substituted or substituted with 1 to 19 fluorine atoms; $X^1$ represents a halogen atom or an alkyl group having 1 to 3 carbon atoms; $X^2$ represents hydrogen atom, a halogen atom or an alkyl group having 1 to 3 carbon atoms; $Y^1$ represents hydrogen atom or fluorine atom; and $Y^2$ represents hydrogen atom or fluorine atom, and herbicidally acceptable carrier and/or adjuvant.

* * * * *

UNITED STATES PATENT AND TRADEMARK OFFICE
CERTIFICATE OF CORRECTION

PATENT NO. : 4,983,209

DATED : January 8, 1991

INVENTOR(S) : Takafumi SHIDA et al

It is certified that error appears in the above-identified patent and that said Letters Patent is hereby corrected as shown below:

On the title page, after "[73] Assignee: Kureha Kagaku Kogyo Kabushiki Kaisha, Tokyo, Japan" insert --[*] Notice: The portion of the term of this patent subsequent to April 11, 2006 has been disclaimed.--

Signed and Sealed this

Sixteenth Day of November, 1993

*Attest:*

BRUCE LEHMAN

*Attesting Officer*   *Commissioner of Patents and Trademarks*